United States Patent [19]

Mukai

[11] Patent Number: 5,163,925
[45] Date of Patent: Nov. 17, 1992

[54] VENTILATION PLUGS FOR TREATMENT OF MIDDLE-EAR DISEASE

[76] Inventor: Susumu Mukai, 8-9 Yamato-Minami 2-Chome, Yamato-shi, Kanagawa-ken, Japan

[21] Appl. No.: 615,282

[22] Filed: Nov. 19, 1990

[30] Foreign Application Priority Data

Nov. 22, 1989 [JP] Japan .................................. 1-301838

[51] Int. Cl.$^5$ .................................................. A61M 5/00
[52] U.S. Cl. ........................................ 604/264; 128/864
[58] Field of Search ............... 128/864, 865, 867, 868; 604/264, 28, 266, 269

[56] References Cited

U.S. PATENT DOCUMENTS

| | | | |
|---|---|---|---|
| 3,530,860 | 9/1970 | Marton | 604/264 |
| 4,094,303 | 6/1978 | Johnston | 128/868 |
| 4,168,697 | 9/1979 | Cantekin | 128/867 |
| 4,326,512 | 4/1982 | Peerless | 128/868 |
| 4,971,076 | 11/1990 | Densert | 604/264 |

OTHER PUBLICATIONS

Richards Price List No. 1584 Oct. 1982.

*Primary Examiner*—Robert A. Hafer
*Assistant Examiner*—David J. Kenealy
*Attorney, Agent, or Firm*—Larson and Taylor

[57] ABSTRACT

A ventilation plug is provided for the treatment of middle-ear diseases. The ventilation plug comprises a front edge portion tapered at an acute angle and an intermediate portion made of water repellent synthetic resin. The intermediate portion is arranged for engagement with the eardrum of a patient. The ventilation plug is designed so as to have a minimized size and thus, the insertion to the eardrum can be executed readily and easily; and the plug is also designed to be air permeable and water repellant.

7 Claims, 2 Drawing Sheets

FIG.I

VENTILATION PLUGS FOR TREATMENT OF MIDDLE-EAR DISEASE

BACKGROUND OF THE INVENTION

The present invention relates to a ventilation plug, for treatment of middle-ear diseases, which is inserted into a middle-ear cavity through the eardrum of a patient.

It is known that hollow ventilation tubes of various types have been employed for the treatment of exudative tympanitis. In operation, the ventilation tubes are inserted into a cut slit in the eardrum of the patient. The slit allows for communication between the middle ear and outside and thus, introduction of atmospheric pressure so that any liquid remaining in the middle ear can be easily removed through an auditory meatus. The draining of liquid is necessary for the prevention of auditory diseases while the eardrum is kept free from deformation.

Each of the prior art ventilation tubes for treatment of middle-ear diseases, e.g. exudative tympanitis, incorporates a hollow space therein. This hollow space allows germs, polluted air, or filthy water from the outside to directly flow into the middle ear and cause inflammation. Hence, the patient who utilizes a conventional ventilation tube has to wear additional protection devices, e.g. ear plugs, for preventing any unwanted object such as water from entering the middle ear during bathing, hair washing, swimming, etc. Also, dirt or dust may enter the middle ear while participating in sports activities.

Consequently, sports players, namely swimmers, and people who work in a dusty atmosphere will be inhibited from carrying out their activities when wearing conventional tubes for the treatment of the middle-ear diseases.

Further, the prior art ventilation tubes are large in cross sectional area and require a slit of extensive size in the eardrum. This slit is for insertion into the middle ear, and causes additional pain to the patient. In some cases, this slit may cause an unacceptable amount of bleeding. It is well understood that the insertion of such a stout ventilation tube can only be executed by a skilled, experienced doctor. The insertion of such a device will be very difficult in the case of a patient who has a small auditory meatus and may even be impossible in some cases.

Conventional ventilation tubes allow the air to pass through a hollow passage therein, and thus offer a ventilation effect. Sometimes, the passage becomes fouled with blood and pus, and thus renders the device unusable. Furthermore, the conventional ventilation tube will provide, due to its size and shape, feelings of an auditory fault and annoyance to the patient who utilizes it. This in turn cause the patient to suffer from mental stress and physical pain a few days after the insertion. It should be noted that about 80% of the patients suffering from the exudative tympanitis are children. Accordingly, such disadvantages in conventional ventilation tubes will seriously undermine therapeutic treatment.

SUMMARY OF THE INVENTION

It is therefore an object of the present invention to overcome the disadvantages involved in conventional ventilation tubes and to provide a ventilation plug for treatment of a middle-ear disease which can be easily inserted by a doctor, be less painful to a patient while in use, provide almost no feelings of an auditory fault or annoyance, and ensure that blood and pus will not affect the operation of the device, while also preventing the invasion of water or dirt from the outside.

According to the present invention, there is provided a ventilation plug for treatment of middle-ear diseases, comprising a body which has two end portions which are tapered at an acute angle, and an intermediate portion. The intermediate portion is for engaging the eardrum of a patient and is made of a water repellent synthetic resin.

Preferably, the body may be shaped in a double wedge configuration in which the body is wedge shaped in two perpendicular planes, e.g. the horizontal and vertical planes. Also, the plug body has opposite edges at each end portion, each of which may be formed in a slightly arcuate shape and rounded off at each corner.

With the ventilation plug for treatment of middle-ear diseases according to the present invention, the plug body is formed of the water repellent synthetic resin material. This material serves as a plug to block water while passing air, i.e. it is made of an air permeable material, thus preventing the invasion of germs, water, dirt, or the like from the outside without losing air permeability.

Also, the ventilation plug according to the present invention can easily be inserted and orientated in a slit by gripping either end of the wedge with a forcep. The ventilation plug may be positioned so that the slit in the eardrum will accept the intermediate portion of the ventilation plug. The plug is secured by the surrounding tissues only a few hours after the insertion and thus prevented from further movement.

The present invention will now be described by way of example with reference to the accompanying drawings.

DETAILED DESCRIPTION

Figure 1:
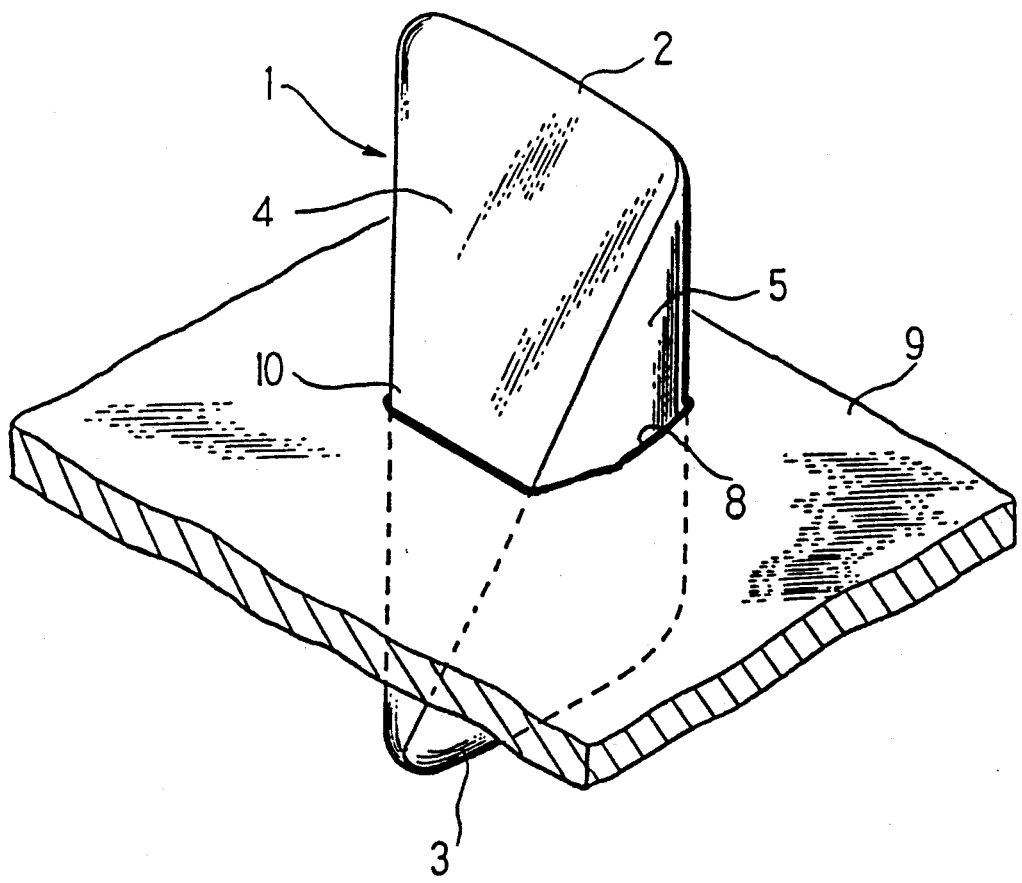
FIG. 1. is an enlarged perspective view showing a preferred embodiment of the present invention.
Figure 2:
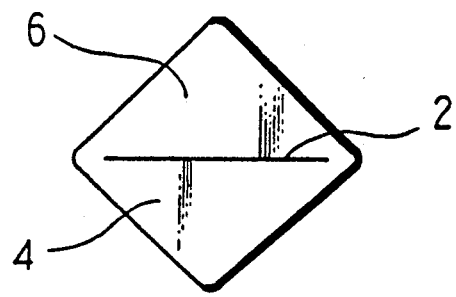
FIG. 2. is a plan view of a ventilation plug shown in FIG. 1.
Figure 3:
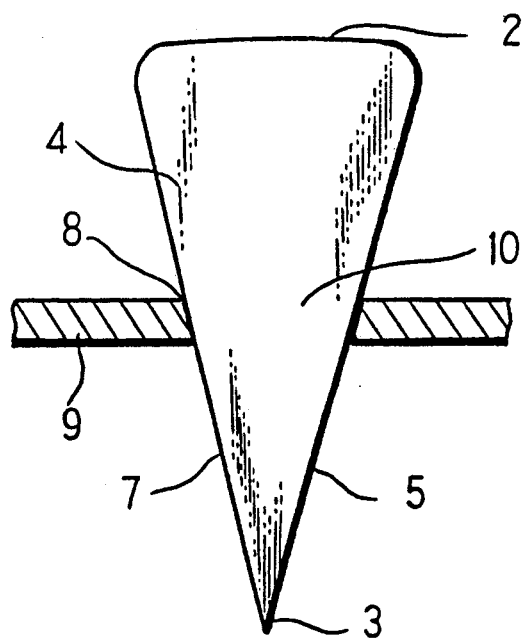
FIG. 3. is a front view of the ventilation plug shown in FIG. 1.

With reference to FIGS. 1 to 3 there is shown a ventilation plug according to the preferred embodiment of the present invention. The illustrated ventilation plug comprises a plug body 1 which is formed of a suitable water repellent synthetic resin material having a wedge shape tapering from one end to the other. The plug body 1 is tapered from one end portion 2 to the other end portion 3 forming a first wedge configuration and also, from the end portion 3 to the end portion 2 forming a second wedge configuration. Thus, the body has a wedge shape in both a horizontal and vertical plane. The first and second wedge configurations are arranged in opposite directions along two planes respectively which extend at a right angle to each other, and are defined by four side surfaces 4 to 7. These side surfaces 4 to 7 are substantially the same in shape, an isosceles triangle. The edge of each of the end portions 2 and 3 is formed in slightly arcuate shape and rounded off at each corner for reducing the resistance to be generated when the plug is inserted into a cut slit 8 in the eardrum 9 of a patient.

Preferably, the ventilation plug may be manufactured using a suitable molding means.

In operation, the ventilation plug described and illustrated in the drawings is gripped at one end by forceps and inserted with the other end forward into a slit 8, which has been provided by cutting a slit of about 1 to 1.5 mm in the eardrum 9 of the patient, until the intermediate portion 10 of the plug body 1 comes into engagement with the slit 8 in the eardrum 9. In this case, the intermediate portion 10 of the plug body 1 is minimum in diameter because each of the four side surfaces is gradually widened from one end portion 2 or to the other end portion 3 or 2 and thus, the intermediate portion 10 acts as an engaging portion for close engagement with the eardrum 9. Both edges of the end portions 2 and 3 extend at a right angle to each other and when any one of the end portions 2 and 3 is gripped by the forceps, the directional position of the other end portion can be easily determined. In this way, the positioning of the ventilation plug 1 to slit 8 in the eardrum 9 may be performed easily. In addition, the wedge shaped ventilation plug can be smoothly inserted into slit 8 in the eardrum 9 with less resistance and more particularly. This allows plug insertion without giving unwanted pain to the patient. In a similar fashion, the removal of the ventilation plug may also be carried out with ease, due to the wedge shape.

Although the illustrated ventilation plug has the arrangement of two wedges tapering in opposite directions to the front and rear, it may have one end or a front end thereof arranged in wedge or cone shape having a sharp edge or point and also, the plug may have a recess or annular slot in the intermediate portion thereof for engagement with the slit in the eardrum.

The illustrated ventilation plug is formed of water repellent fluorocarbon resin. However, only the center portion or the intermediate portion of the ventilation plug may be formed of water repellent fluorocarbon resin and the remaining portions thereof may be formed of other suitable material.

Further, with the illustrated embodiment each of the four side surfaces of the ventilation plug may have an outwardly curved shape. Also, the wedge shapes extending from the opposite ends may be arranged at a given angle, other than a right angle, to each other.

An example of the ventilation plug will now be described referring to the results of clinical use in forty-two patients suffering from exudative tympanitis.

Ventilation plugs each having wedge shape of 3 mm long, 1 mm wide and 0.5 mm thick at the front edge and made of water repellent polytetorafluoroethylene in accordance with the present invention, were made.

The insertion of the ventilation plug into the eardrum of each of the 42 outpatients was performed using ion anesthesia. The remaining period of the inserted ventilation plug in the eardrum was 262 days at maximum, 3 days at minimum, and 86 days in average in which the standard deviation was 61.5. With each of the patients, an improvement in the sense of hearing achieved after the insertion of the ventilation plug.

Therefore, the present invention has an advantage that corresponding clinical operations will be facilitated while causing no pain to the patients, as compared with conventional treatments. The present invention also has the advantages that there will be provided less sense of annoyance after insertion of the ventilation plug to the patient and that there will be ensured a balance between the interior pressure and atmospheric pressure.

Further, according to the ventilation plug of the present invention, it is possible to prevent any invasion of unwanted substances such as water and epidemic germs, thus allowing the patient to carry out activities such as washing his or her hair during bathing or swimming.

Furthermore, the present invention has an advantage that, being of air permeable material, it can provide a continuous (air) ventilation effect to allow undesired liquids to flow out from the middle ear while being substantially unaffected by blood and pus derived from the affected part of a middle ear disease.

Additionally, the ventilation plug according to the present invention has no hollow tubular shaped members and will thus be formed into a more adaptable shape.

It is to be understood that the present invention is not limited to the particular embodiments described and illustrated and that numerous modifications and alterations may be made by those skilled in the art without departing from the spirit and scope of the invention.

I claim:

1. A ventilation plug for treatment of middle-ear diseases comprising; a solid body which has opposed end portions, each being tapered at an acute angle, said solid body being shaped in a double wedge configuration in which two opposite sides are tapered in one direction from one end to the other, and the other two opposite sides are tapered in a second direction perpendicular to the first direction, and an intermediate portion for engagement with the eardrum of a patient, at least said intermediate portion being a solid structure made of an air permeable and water repellent material.

2. A ventilation plug according to claim 1, wherein the entire said body is made of an air permeable water repellant synthetic resin.

3. A ventilation plug according to claim 1, wherein said body has opposite edges at each end portion, each of which is slightly arcuate in shape and rounded off at each corner.

4. A ventilation plug according to claim 3, wherein said edges are positioned at a right angle to each other.

5. A ventilation plug for treatment of middle-ear diseases comprising, a body which has opposed end portions, each being tapered at an acute angle, said body being shaped in a double wedge configuration in which two opposite sides are tapered in one direction from one end to the other, and the other two opposite sides are tapered in a second opposite direction perpendicular to the first direction; and an intermediate portion for engagement with the eardrum of a patient, at least said intermediate portion being made of water repellent synthetic resin.

6. A ventilation plug according to claim 5, wherein said body has opposite edges at each end portion, each of which is slightly arcuate in shape and rounded off at each corner.

7. A ventilation plug according to claim 6, wherein said edges are positioned at a right angle to each other.

* * * * *